United States Patent

Ueda et al.

[11] Patent Number: 5,962,453
[45] Date of Patent: *Oct. 5, 1999

[54] TRIAZINE DERIVATIVE AND MEDICINE

[75] Inventors: Fusao Ueda; Takayuki Ozaki, both of Shiga; Ken-ichi Nakamura, Kyoto, all of Japan

[73] Assignee: Nippon Shinyaku Co. Ltd., Kyoto, Japan

[*] Notice: This patent is subject to a terminal disclaimer.

[21] Appl. No.: 08/776,992

[22] PCT Filed: Aug. 8, 1995

[86] PCT No.: PCT/JP95/01577

§ 371 Date: Feb. 6, 1997

§ 102(e) Date: Feb. 6, 1997

[87] PCT Pub. No.: WO96/04914

PCT Pub. Date: Feb. 22, 1996

[51] Int. Cl.[6] ............ A01N 43/66; C07D 251/00
[52] U.S. Cl. ............ 514/245; 544/194; 544/208
[58] Field of Search ............ 544/194, 208; 514/245

[56] References Cited

U.S. PATENT DOCUMENTS

| | | | |
|---|---|---|---|
| 4,103,009 | 7/1978 | Murai et al. | 424/249 |
| 4,333,933 | 6/1982 | Matsumura et al. | 424/249 |
| 4,487,770 | 12/1984 | Enomoto et al. | 424/249 |
| 4,554,275 | 11/1985 | Sempuku et al. | 514/245 |

FOREIGN PATENT DOCUMENTS

| | | |
|---|---|---|
| 066799 | 12/1982 | European Pat. Off. . |
| 66799 | 12/1982 | European Pat. Off. . |
| WO91-1733 | of 1984 | WIPO . |

OTHER PUBLICATIONS

Mizoguchi et al, Gastroenterol. Jpn., 26(2), 177–181 (1991).
Derwent Abstract of WO91–1733, 1984.

*Primary Examiner*—Richard L. Raymond
*Assistant Examiner*—Tamthom T. Ngo
*Attorney, Agent, or Firm*—Graham & James LLP

[57] ABSTRACT

The invention relates to a medicinal composition comprising a triazine derivative of the following general formula [I]

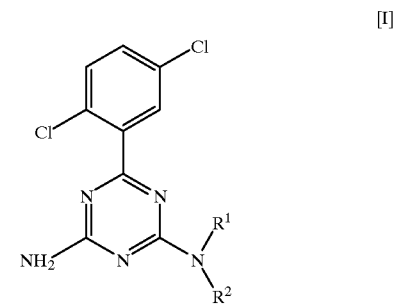

or a solvate thereof, or a salt thereof, as an active ingredient. In the above formula, $R^1$ and $R^2$ may be the same or different and each represents hydrogen, unsubstituted or substituted alkyl aralkyl, or alkenyl, or jointly represent cyclic amino ($NR^1R^2$) in combination with the adjacent nitrogen atom. The cyclic amino may contain nitrogen, oxygen, or sulfur as a ring member in addition to the adjacent nitrogen and may be further substituted. Excluded is the case in which $NR^1R^2$ is $NH_2$. The compound of the invention is useful as a therapeutic drug for hepatitis.

18 Claims, No Drawings

TRIAZINE DERIVATIVE AND MEDICINE

This is a 371 application of PCT/JP 95/01574 filed on Aug. 8, 1995.

TECHNICAL FIELD

The present invention relates to a triazine derivative useful as a medicine.

BACKGROUND ART

Hepatitis is etiologically classified into viral hepatitis (hepatitis A, B, and C, multiple infection hepatitis, etc.), toxic hepatitis (e.g. drug-induced), and autoimmune hepatitis.

Among them there are hepatitis which frequently follows a subchronic to chronic course (acute hepatitis C) and refractory hepatitis characterized by recurrent episodes of acute exacerbation and ultimate progression to cirrhosis (chronic hepatitis B). There also is hepatitis which follows a precipitating course, that is fulminant hepatitis.

The treatment of hepatitis includes, in addition to the general therapy for encouraging the mechanism of cure based on rest and diet therapy, antiviral therapy which is instituted for inhibiting growth of the causative virus in cases of viral hepatitis and immunotherapy for potentiating the compromised cellular immunity of the host. The liver drugs available are liver hydrolyzate, glycyrrhizin, reduced glutathione, tiopronin, and polyenephosphatidylcholine, among others. As antiviral aagents, interferons, arabinosyladenine (Ara—A), arabinosyladenosine monophosphate (Ara—AMP), acyclovir, etc. are used. As immunoregulators, glucocorticoids, interleukin-2, picibanil (OK-432), cianidanol, levamisol, etc. are used. Interferons have immunological actions in addition to antiviral activity. Prostaglandin E is known to have a cytoprotective action and is expected to be useful for protection of liver cells. Aside from the foregoing drugs, human epidermal growth factor (hEGF) and human hepatocyte growth factor (hHGF) are known to have cytogenesis promoting activity and their clinical application as liver regeneration promoting factors is considered promising but they are still in the stage of preclinical study.

Recently, vaccine therapy has been recommended for the treatment and prevention of hepatitis B.

However, no satisfactory therapeutic drug for hepatitis is available as yet and there is a standing need for the creation of a drug effective for preventing extensive necrosis and enhancing regeneration of hepatocytes.

It is known that irsogladine maleate (2,4-diamino-6-(2,5-dichlorophenyl)-1,3,5-triazine maleate), which is a benzoguanamine derivative structurally analogous to the compound of the present invention and such that the 2- and 5-positions of phenyl moiety of benzoguanamine have been substituted by chlorine, with both the two amino groups being unsubstituted, has a hepatocyte-protective action and is useful for the treatment of hepatitis (See Japanese Kokai Tokkyo Koho S58-55423, WO 91/01733). Similarly, derivatives also having a 2,5-dichlorophenyl group but having a piperidino or morpholino group in lieu of one of said amino groups, namely 2-amino-4-(2,5-dichlorophenyl)-6-piperidino-1,3,5-triazine and 2-amino-4-(2,5-dichlorophenyl)-6-morpholino-1,3,5-triazine, are known as intermediates for the preparation of antiallergic nicotinoyl-benzoguanamine derivatives (Japanese Kokai Tokkyo Koho S57-203083 and S59-104320). Meanwhile, there is a host of known compounds corresponding to benzoguanamine, the phenyl moiety of which is either unsubstituted or halogenated and one of the amino groups of which is substituted. As an example of the compound having an acyclic group substituting one of said amino groups, amino-4-(2-hydroxyethylamino)-6-phenyl- 1,3,5-triazine can be mentioned. This compound reportedly is useful as a starting material for production of resins (CA 106:34062). As a compound having a cyclic amino group, 2-amino-4-(4-methylpiperazin-1-yl)-6-phenyl-1,3,5-triazine is known to have an analgesic action (CA 84:135722). However, as to compounds corresponding to benzoguanamine in which both the 2- and 5-positions of its phenyl moiety are substituted by chlorine and one of the amino groups is a substituted amino group, there is no known compound except said compounds substituted by either piperidino or morpholino for one of the amino groups.

DISCLOSURE OF INVENTION

The present invention has for its object to provide a triazine derivative having a novel structure and a low toxic potential and showing efficacy in hepatitis and a useful medicinal composition comprising the derivative as an active ingredient.

To accomplish the above object, the inventors of the present invention synthesized and studied a variety of structurally novel compounds and found that compared with irsogladine maleate, namely [2,4-diamion-6-(2,5-dichlorophenyl)-1,3,5-triazine maleate], which is disclosed in Japanese Kokai Tokkyo Koho S58-55423 and WO 91/01733 referred to above, the compound of the following general formula [I] exhibits remarkably superior anti-hepatitis and hepatic oncogenesis-inhibitory activity in mammalian animals, with low toxicity, and, hence, is useful as a therapeutic agent for hepatitis. The present invention has been completed on the basis of the above finding.

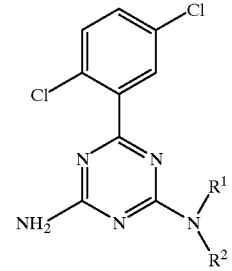

[I]

The present invention relates, in a first aspect, to a medicinal composition comprising a compound of the above general formula [I] or a solvate thereof, or a salt thereof, as an active ingredient and, in a second aspect, to said compound of general formula [I], solvate, or salt.

In the above general formula, $R^1$ and $R^2$ may be the same or different and each represents hydrogen, unsubstituted or substituted alkyl, aralkyl, aralkenyl, or aryl, or $R^1$ and $R^2$, jointly and taken together with the adjacent N atom, represent a 4- through 8-membered cyclic amino group as the formula $NR^1R^2$. The cyclic amino group may contain, in addition to the above-mentioned N atom, nitrogen, oxygen, or sulfur as a ring member and may be further substituted.

The structural feature of this compound resides in that both the 2- and 5-positions of the phenyl moiety of benzoguanamine are substituted by chlorine and one of the amino groups of guanamine is free, with the other being substituted.

The compound of the above general formula [I] is a novel compound never heretofore described, except species such that both $R^1$ and $R^2$ represent hydrogen and species such that $NR^1R^2$ represents piperidino or morpholino. These species are known compounds and are, therefore, not included in the scope of the compound claim of the present invention. However, the remarkable anti-hepatitis activity of these species was discovered for the first time by the inventors of the present invention and, therefore, are included in the scope of the composition claims of the present invention.

The present invention is now described in detail.

The alkyl for $R^1$ and $R^2$ may be a straight-chain or branched-chain of 1-10 carbon atoms, such as methyl, ethyl, n-propyl, isopropyl, n-butyl, isobutyl, secbutyl, tert-butyl, n-pentyl, isopentyl, n-hexyl, isohexyl, n-heptyl, isoheptyl, n-octyl, isooctyl, n-nonyl, isononyl, n-decyl, and isodecyl. Preferred are $C_{1-4}$ alkyl groups. The alkyl may be substituted by 1–3 substituent groups, either the same or different, as selected from the group consisting of hydroxy, alkoxy, amino, monoalkylamino, dialkylamino, arylamino, cyclic amino, carboxy, carbamoyl, aryloxy, and aroyloxy. Particularly preferred is hydroxy. When the substituent group has an aryl moiety, the latter may be substituted by $C_{1-4}$ alkyl or alkoxy.

The substituted alkyl includes but is not limited to the following groups.

The hydroxyalkyl includes 2-hydroxyethyl, 3-hydroxypropyl, 2-hydroxypropyl, 4-hydroxybutyl, 3-hydroxybutyl, 5-hydroxypentyl, 6-hydroxyhexyl, 7-hydroxyheptyl, 8-hydroxyoctyl, 9-hydroxynonyl, 10-hydroxydecyl, etc.

The alkoxy of the alkoxyalkyl may be a straight-chain or branched-chain of 1-4 carbon atoms, such as methoxy, ethoxy, n-propoxy, isopropoxy, n-butoxy, isobutoxy, sec-butoxy, tert-butoxy, etc. The alkoxyalkyl specifically includes 2-methoxyethyl, 3-methoxypropyl, 2-methoxypropyl, 4-methoxybutyl, 3-methoxybutyl, 5-methoxypentyl, 6-ethoxyhexyl, 7-ethoxyheptyl, 8-ethoxyoctyl, 9-propoxynonyl, and 10-propoxydecyl.

The aminoalkyl includes 2-aminoethyl, 3-aminopropyl, 2-aminopropyl, 4-aminobutyl, 3-aminobutyl, 5-aminopentyl, 6-aminohexyl, 7-aminoheptyl, 8-aminooctyl, 9-aminononyl, and 10-aminodecyl.

The monoalkylaminoalkyl includes 2-methylaminoethyl, 3-methylaminopropyl, 4-methylaminobutyl, 3-ethylaminopropyl, 3-ethylaminobutyl, 5-ethylaminopentyl, 6-ethylaminohexyl, 7-propylaminoheptyl, 8-propylaminooctyl, 9-butylaminononyl, and 10-butylaminodecyl.

The dialkylaminoalkyl includes 2-(N,N-dimethylamino)ethyl, 3-(N,N-dimethylamino)propyl, 4-(N,N-dimethylamino)butyl, 3-(N,N-diethylamino)propyl, 3-(N,N-diethylamino)butyl, 5-(N,N-diethylamino)pentyl, 6-(N,N-diethylamino)hexyl, 7-(N,N-dipropylamino)heptyl, 8-(N,N-dipropylamino)octyl, 9-(N,N-dibutylamino)nonyl, and 10-(N,N-dibutylamino)decyl.

The arylamino moiety of the arylaminoalkyl includes anilino and naphthylamino, among others.

The cyclic amino moiety of the cyclic aminoalkyl includes the 4- through 8-membered cyclic groups mentioned hereinafter for $NR^1R^2$. Particularly preferred are piperidino, piperazinyl, and morpholino. The cyclic amino moiety may be substituted by $C_{7-13}$ aralkyl.

The carboxyalkyl includes 1-carboxymethyl, 2-carboxyethyl, 3-carboxypropyl, 2-carboxypropyl, 4-carboxybutyl, 3-carboxybutyl, 5-carboxypentyl, 6-carboxyhexyl, 7-carboxyheptyl, 8-carboxyoctyl, 9-carboxynonyl, and 10-carboxydecyl.

The carbamoylalkyl includes 1-carbamoylmethyl, 2-carbamoylethyl, 3-carbamoylpropyl, 2-carbamoylpropyl, 4-carbamoylbutyl, 3-carbamoylbutyl, 5-carbamoylpentyl, 6-carbamoylhexyl, 7-carbamoylheptyl, 8-carbamoyloctyl, 9-carbamoylnonyl, and 10-carbamoyldecyl.

The aryl moiety of the aryloxyalkyl includes $C_{6-13}$ aryl groups, such as phenyl, 1-naphthyl, 2-naphthyl and biphenyl. Particularly preferred is phenyl.

The aroyl moiety of the aroyloxyalkyl includes $C_{7-10}$ groups such as benzoyl and nicotinoyl, among others. Particularly preferred is benzoyl.

The aralkyl includes $C_{7-14}$ groups such as benzyl, phenethyl, phenylpropyl, phenylbutyl and diphenylmethyl.

The aralkenyl includes $C_{7-10}$ groups such as cinnamyl and 3-phenylallyl, among others.

The aryl includes those groups mentioned above for the aryl moiety of the aryloxy. Particularly preferred is phenyl.

Referring to the above-mentioned substituent groups containing an aryl moiety, the aryl moiety may be substituted by 1–3 alkyl or alkoxy groups, either the same or different, each containing 1–4 carbon atoms.

The 4- through 8-membered cyclic amino represented with $NR^1R^2$ includes azetidin-1-yl, pyrrolidin-1-yl, 3-pyrrolin-1-yl, piperidino, hexamethyleneimino, octahydroazocin-1-yl, piperazin-1-yl, homopiperazin-1-yl, morpholino, and thiomorpholino, among others. Preferred are 5- or 6-membered cyclic amino groups. Particularly preferred is pyrrolidin-1-yl, piperidino, or morpholino. The cyclic amino group may be substituted by 1–4 substituent(s) selected from the group consisting of hydroxy, oxo, carboxy, alkyl, hydroxyalkyl, aryloxyalkyl, aminoalkyl, alkylsulfonylaminoalkyl, alkylsulfonylamino, alkylsulfonylaralkyl, alkylsulfonyl, aryl, aralkyl, 2-pyrimidinyl, and cyclic amino. The alkyl in such a substituent group may be any of said straight-chain or branched-chain alkyl groups of 1–4 carbon atoms. The aryl in such a substituent group may be any of the $C_{6-12}$ aryl groups mentioned hereinbefore. This aryl may be substituted by $C_{1-4}$ alkyl or alkoxy. Particularly preferred substituents for the cyclic amino group $NR^1R^2$ are hydroxy, hydroxyalkyl, oxo, amino, and alkyl.

The salt of compound [I] which falls within the scope of the invention includes salts with mineral acids such as hydrochloric acid, sulfuric acid, nitric acid, phosphoric acid, hydrofluoric acid and hydrobromic acid, and salts with organic acids such as acetic acid, tartaric acid, lactic acid, citric acid, fumaric acid, maleic acid, succinic acid, methanesulfonic acid, ethanesulfonic acid, benzenesulfonic acid, toluenesulfonic acid, naphthalenesulfonic acid and camphorsulfonic acid.

The compound [I] of the present invention can be obtained, for example by the following process.

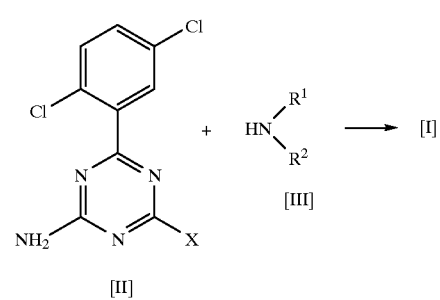

Thus, compound [I] can be prepared by reacting a halotriazine derivative [III] (wherein X represents chlorine or fluorine) with an amine [III] in the presence of a base in a solvent inert to the reaction at 0–200° C., preferably 25–100° C. The reaction solvent that can be used includes aprotic polar solvents such as acetonitrile, dimethyl sulfoxide and N,N-dimethylformamide (DMF), ethers such as tetrahydrofuran, dimethoxyethane, diethyl ether and dioxane, glymes such as methylcellosolve and ethylene glycol dimethyl ether, halogenated hydrocarbons such as methylene chloride and chloroform, hydrocarbons such as benzene, toluene and xylene, and mixtures of such solvents. The base that can be used includes inorganic bases such as alkali metal carbonates (e.g. potassium carbonate, sodium carbonate), alkali metal hydrogen carbonates (e.g. potassium hydrogen carbonate, sodium hydrogen carbonate), and alkali metal hydroxides (e.g. potassium hydroxide, sodium hydroxide), and organic bases such as triethylamine and pyridine. In lieu of the base, the amine ($HNR^1R^2$) may be used in excess.

The reaction time depends on the species of starting compounds, base, and solvent used but generally may range from several minutes to 24 hours.

The proportion of amine [III] to be used is at least equimolar, preferably 1–1.2 molar equivalents, to each mole of [III]. The proportion of the base to be used is at least equimolar, preferably 1–2 molar equivalents, to each mole of [III].

The starting compound [III] can be prepared by known method (Japanese Kokai Tokkyo Koho S51-70781). [III] may be a commercially available or can be synthesized typically as shown in the reference examples hereinafter.

While some of the compound [I] contain one or more asymmetric carbon atoms and, therefore, may exist as optically active forms, the respective isomers and optional mixtures thereof are also included in the scope of the present invention.

The optically active compounds mentioned above can be resoluted optically from mixtures by known method, for example by using a chiral column or by using a chiral acid (e.g. tartaric acid, dibenzoyl tartrate, mandelic acid, 10-camphorsulfonic acid) by taking advantage of their basicity. As an alternative, the optically active compounds can be obtained by using an optically active compound [III] prepared beforehand as a starting material.

The compound [I] of the present invention can be treated in the per se known manner to form any of the above-mentioned salts. For example, the hydrochloride of compound [I] can be obtained by dissolving compound [I] in an alcoholic solution of hydrogen chloride.

Among species of compound [I] according to the present invention, any compound having a carboxyl group can be converted to a salt by the known process. The salt here includes alkali metal salts such as sodium salt and potassium salt, and alkaline earth metal salts such as calcium salt. An alkali metal salt of compound [I] of the invention can be obtained by adding one equivalent of sodium hydroxide, potassium hydroxide, or the like to a carboxy-containing compound [I] of the invention, preferably in an alcoholic solvent. An alkaline earth metal salt of compound [I] of the invention can be obtained by dissolving the above alkali metal salt in water, methanol, ethanol, or a mixture thereof, for instance followed by adding one equivalent of, for example, calcium chloride.

The solvate (inclusive of the hydrate) of the compound [I] or salt of the invention is also included in the scope of the present invention. The solvate can be generally obtained by recrystallizing the compound from the corresponding solvent or a suitable mixed solvent containing the corresponding solvent. For example, the hydrate of compound [I] of the present invention can be obtained by recrystallizing compound [I] from an aqueous alcohol.

Compound [I] of the present invention may show crystal polymorphism. The polymorphs are also included in the scope of the invention.

The desired compound [I] thus obtained can be isolated and purified by per se known procedures such as concentration, pH adjustment, phase transfer, solvent extraction, crystallization, fractional distillation, and chromatography.

The compound of the present invention is useful as a therapeutic drug for hepatitis.

For use as a medicine, the compound of the present invention is administered as it is or in the form of a pharmaceutical composition containing, for example, 0.1–99.5%, preferably 0.5–90%, of the compound in a pharmaceutically acceptable nontoxic, inert carrier.

As the carrier, one or more of solid, semisolid, or liquid diluent, filler, and other formulation auxiliaries can be employed. The pharmaceutical composition is preferably administered in unit dosage forms. The pharmaceutical composition of the present invention can be administered orally, parenterally, locally (e.g. transdermally), or rectally. Of course, dosage forms suited for respective routes of administration should be selected. Particularly preferred is oral administration.

The dosage as a therapeutic drug for hepatitis is preferably established with reference to the age, body weight and other patient factors, route of administration, nature and severity of illness, etc. Usually, however, the daily oral dosage for adult humans may range generally from 100 $\mu$g to 100 mg/patient and preferably from 500 $\mu$g to 30 mg/patient. Lower dose levels may be sufficient in some cases, while higher dose levels may be necessary in other cases. The above-mentioned dosage can be administered in 2–3 divided doses where necessary.

Oral administration can be carried out using solid or liquid dosage forms such as bulk powders, powders, tablets, dragees, capsules, granules, suspensions, solutions, syrups, drops and sublingual tablets.

Bulk powders can be manufactured by comminuting the active substance into a finely divided form.

Powders can be manufactured by comminuting the active substance into a finely-divided form, followed by blending it with a similarly comminuted pharmaceutical carrier, e.g. an edible carbohydrate such as starch or mannitol. Where necessary, a corrigent, a preservative, a dispersant, a coloring matter, a flavor, etc. can also be added.

Capsules can be manufactured by filling said finely-divided bulk powders, powders or granules described for tablets in capsule shells such as gelatin capsule shells. Preceding the filling operation, a lubricant or a fluidizing agent, such as colloidal silica, talc, magnesium stearate, calcium stearate or solid polyethylene glycol, can be blended with the powders. Improvement in the efficacy of the drug after ingestion can be achieved when a disintegrator or a solubilizer, such as carboxymethylcellulose, carboxymethylcellulose calcium, low-substitution-degree hydroxypropylcellulose, croscarmellose sodium, carboxymethylstarch sodium, calcium carbonate or sodium carbonate, is added.

Soft capsules can be manufactured by suspending said finely divided powders in vegetable oil, polyethylene glycol, glycerin, or a surfactant and wrapping the suspension in gelatin sheets. Tablets can be manufactured by adding an excipient to said powders, granulating or slugging the mixture, adding a disintegrator or a lubricant, and compressing the whole composition. A powdery mixture can be prepared by mixing said finely divided powders with said diluent or base. Where necessary, a binder (e.g. carboxymethylcellulose sodium, methylcellulose, hydroxypropylmethylcellulose, gelatin, polyvinylpyrrolidone, polyvinyl alcohol, etc.), a dissolution retardant (e.g. paraffin), a reabsorption agent (e.g. quaternary salts), and an adsorbent (e.g. bentonite, kaolin, dicalcium phosphate, etc.) can be added. The powdery mixture can be processed into granules by wetting it with a binder, e.g. a syrup, a starch paste, gum arabic, a solution of cellulose, or a solution of a high polymer, stirring the mixture, drying it, and pulverizing the same. Instead of granulating such powders, it is possible to compress the powders with a tablet machine and crush the resulting slug of crude form. The resulting granules can be protected against inter-adhesion by the addition of a lubricant such as stearic acid, a salt of stearic acid, talc, mineral oil, or the like. The mixture thus lubricated is then compressed. The resulting uncoated tablets can be coated with a film coating composition or a sugar coating composition.

The drug can be mixed with a free-flowing inert carrier and the mixture be directly compressed without resort to the above-mentioned granulation or slugging process. A transparent or translucent protective coat consisting in, for example, a hermetic shellac coat, a sugar or polymer coat, or a polishing wax coat can also be applied. Other oral compositions such as a solution, a syrup, and an elixir can also be provided in unit dosage forms each containing a predetermined proportion of the drug substance. Syrups can be manufactured by dissolving the compound in suitable flavored aqueous solutions, while elixirs can be manufactured using nontoxic alcoholic vehicles. Suspensions can be formulated by dispersing the compound in nontoxic vehicles. Where necessary, solubilizers and emulsifiers (e.g. ethoxylated isostearyl alcohol, polyoxyethylene sorbitol ester, etc.), preservatives, and flavorants (e.g. peppermint oil, saccharin, etc.) can also be added.

Where necessary, the unit dosage formulation for oral administration can be microencapsulated. This formulation can be coated or embedded in a polymer, wax or other matrix to provide a prolonged action or sustained release dosage form.

Parenteral administration can be made using liquid unit dosage forms for subcutaneous, intramuscular, or intravenous injection, e.g. solutions and suspensions. Such unit dosage forms can be manufactured by suspending or dissolving a predetermined amount of the compound in an injectable nontoxic liquid vehicle, for example an aqueous vehicle or an oily vehicle, and sterilizing the resulting suspension or solution. For isotonizing an injection, a nontoxic salt or salt solution can be added. Moreover, stabilizers, preservatives, emulsifiers, etc. may also be added.

Rectal administration can be made by using suppositories manufactured by dissolving or suspending the compound in a low-melting water-soluble or water-insoluble solid carrier such as polyethylene glycol, caccao butter, semisynthetic oil (e.g. Witepsol®), a higher ester (e.g. myristyl palmitate) or a mixture of them.

BEST MODE FOR CARRYING OUT THE INVENTION

The following examples and test examples relating to some representative species of the compound of the invention are intended to describe the present invention in further detail and should by no means be construed as defining the scope of the invention.

REFERENCE EXAMPLE 1

Synthesis of trans-4-hydroxy-L-prolinol.

In 30 ml of dry THF was suspended 1.57 g of lithium aluminum hydride and the solution was cooled to $-10°$ C. To this solution was added a solution of trans-4-hydroxy-L-proline methyl ester (3.00 g) in THF (10 ml) dropwise at a temperature range of $-10°$ to $-5°$ C. The mixture was stirred at room temperature for 2 hours and, then, refluxed for 30 minutes. To this reaction mixture were added ethyl acetate and aqueous THF, and the mixture was filtered. The insoluble matter was washed with THF and the filtrate was concentrated under reduced pressure to provide 2.0 g of yellow oil.

REFERENCE EXAMPLE 2

Synthesis of 3-hydroxymethylazetidine.

In a medium-pressure reduction apparatus of 300 ml capacity, a suspension of 1-diphenylmethyl-3-hydroxymethylazetidine (8.00 g) and 5% Pd/C (2.50 g) in methanol (80 ml) was treated with hydrogen gas at 5.1 kg/cm$^2$ and 50° C. for 15 hours. This reaction mixture was filtered and the separated Pd/C was washed well with methanol. The filtrate and methanol wash were combined and concentrated under reduced pressure. The residue was diluted with about 30 ml of n-hexane and stirred well and the supernatant was decanted off to provide 2.85 g of crude 3-hydroxymethylazetidine.

Similarly, 3.24 g of 3-hydroxyazetidine was synthesized starting with 10.11 g of 1-diphenylmethyl-3-hydroxyazetidine.

REFERENCE EXAMPLE 3

Synthesis of 3-methanesulfonylaminopyrrolidine.
(Step 1)
While a suspension of 3-amino-1-benzylpyrrolidine (7.00 g) and potassium carbonate (6.04 g) in THF (100 ml) was stirred at room temperature, a solution of methanesulfonyl chloride (5.00 g) in THF (40 ml) was added gradually dropwise and the mixture was stirred at room temperature for 20 hours. This reaction mixture was concentrated under reduced pressure and the residue was suspended in ethyl acetate. This suspension was washed with water and saturated aqueous NaCl solution, dehydrated over anhydrous magnesium sulfate (MgSO$_4$) and concentrated. The residual crude product was purified by column chromatography (C-200/trademark; CHCl$_3$→CHCl$_3$:MeOH=30:1) to provide 10.10 g of 1-benzyl-(3-methanesulfonylamino) pyrrolidine as light-brown oil.
(Step 2)
A suspension consisting of 10.00 g of the above compound, 2.00 g of 5% Pd/C, 50 ml of methanol, and 10 ml of acetic acid was prepared in a 300 ml medium-pressure reduction apparatus and treated with hydrogen gas at 5.1 kg/cm$^2$ and 40° C. for 15 hours. This reaction mixture was after-treated as in Reference Example 2 to provide 9.20 g of 3-methanesulfonylaminopyrrolidine.

EXAMPLE 1

Synthesis of 2-amino-4-[N,N-bis(2-hydroxyethyl)amino]-6-(2,5-dichlorophenyl)-1,3,5-triazine.

To a mixture of diethanolamine (9.2 g), N,N-dimethylformamide (200 ml), and anhydrous potassium carbonate (15 g) was added 20 g of 2-amino-4-chloro-6-(2,5-dichlorophenyl)-1,3,5-triazine with stirring at room temperature and the mixture was stirred at room temperature for 7 hours. This reaction mixture was diluted with 2L (litters) of water and stirred for 1 hour. The resulting crystals were collected by filtration, rinsed with water, and dried to give 24 g of white crystals. This crystal crop was recrystallized from methanol, collected by filtration, and dried to provide 21 g of the title compound as white crystals. m.p. 199–200° C.

Elemental analysis for $C_{13}H_{15}Cl_2N_5O_2$. Calcd. (%): C, 45.36; H, 4.39; N, 20.35. Found (%): C, 45.58; H, 4.33; N, 20.46.

EXAMPLE 2

2-Amino-4-(2,5-dichlorophenyl)-6-methylamino-1,3,5-triazine.

Using methylamine in lieu of diethanolamine, the procedure was carried out in the same manner as Example 1 to give the title compound. m.p. 205–206° C.

Elemental analysis for $C_{10}H_9Cl_2N_5$. Calcd. (%): C, 44.47; H, 3.36; N, 25.93. Found (%): C, 44.24; H, 3.30; N, 25.70.

EXAMPLE 3

2-Amino-4-(2,5-dichlorophenyl)-6-dimethylamino-1,3,5-triazine.

Using dimethylamine in lieu of diethanolamine, the procedure was carried out in the same manner as Example 1 to provide the title compound. m.p. 178–179° C.

Elemental analysis for $C_{11}H_{11}Cl_2N_5$. Calcd. (%): C, 46.50; H, 3.90; N, 24.65. Found (%): C, 46.45; H, 3.73; N, 24.39.

EXAMPLE 4

2-Amino-4-(2,5-dichlorophenyl)-6-(2-hydroxyethylamino)-1,3,5-triazine

Using ethanolamine in lieu of diethanolamine, the procedure was carried out in the same manner as Example 1 to provide the title compound. m.p. 198–199° C.

Elemental analysis for $C_{11}H_{11}Cl_2N_5O$. Calcd. (%): C, 44.02; H, 3.69; N, 23.33. Found (%) C, 43.82; H, 3.46; N, 23.01.

EXAMPLE 5

2-Amino-4-(2,5-dichlorophenyl)-6-[N-methyl-N-(2-hydroxyethyl)amino]-1,3,5-triazine Using N-methyl-N-(2-hydroxyethyl)amine in lieu of diethanolamine, the procedure was carried out in the same manner as Example 1 to provide the title compound. m.p. 153–155° C.

Elemental analysis for $C_{12}H_{13}Cl_2N_5O$. Calcd. (%) C, 45.88; H, 4.17; N, 22.29. Found (%) C, 45.60; H, 4.06; N, 22.25.

EXAMPLE 6

2-Amino-4-(2,5-dichlorophenyl)-6-(2-methoxyethylamino)-1,3,5-triazine

Using 2-methoxyethylamine in lieu of diethanolamine, the procedure was carried out in the same manner as Example 1 to provide the title compound. m.p. 195–197° C.

Elemental analysis for $C_{12}H_{13}Cl_2N_5$. Calcd. (%): C, 45.88; H, 4.17; N, 22.29. Found (%) C, 45.72; H, 3.90; N, 22.12.

EXAMPLE 7

2-Amino-4-(2,5-dichlorophenyl)-6-(8-diethylamino-1-octylamino)-1,3,5-triazine

Using 8-diethylamino-1-octylamine in lieu of diethanolamine, the procedure was carried out in the same manner as Example 1 to provide the title compound. m.p. 101–102° C.

Elemental analysis for $C_{21}H_{32}Cl_2N_6$. Calcd. (%): C, 57.40; H, 7.34; N, 19.12. Found (%): C, 57.16; H, 7.48; N, 18.92.

EXAMPLE 8

2-Amino-4-benzylamino-6-(2,5-dichlorophenyl)-1,3,5-triazine

Using benzylamine in lieu of diethanolamine, the procedure was carried out in the same manner as Example 1 to provide the title compound. m.p. 200–201° C.

Elemental analysis for $C_{16}H_{13}Cl_2N_5$. Calcd. (%): C, 55.51; H, 3.78; N, 20.23. Found (%) C, 55.78; H, 3.66; N, 20.07.

EXAMPLE 9

2-Amino-4-(2,5-dichlorophenyl)-6-[4-(2-pyrimidyl)-piperazin-1-yl]-1,3,5-triazine.

Using 4-(2-pyrimidyl)piperazine in lieu of diethanolamine, the procedure was carried out in the same manner as Example 1 to provide the title compound. m.p. 224–225° C.

Elemental analysis for $C_{17}H_{16}Cl_2N_8$. Calcd. (%) C, 50.63; H, 4.00; N, 27.79. Found (%): C, 50.48; H, 3.91; N, 27.92.

EXAMPLE 10

2-Amino-4-(N-benzyl-N-methylamino)-6-(2,5-dichlorophenyl)-1,3,5-triazine.

Using N-methylbenzylamine in lieu of diethanolamine, the procedure was carried out in the same manner as Example 1 to give the title compound. m.p. 163–164° C.

Elemental analysis for $C_{17}H_{15}Cl_2N_5$. Calcd. (%): C, 56.68; H, 4.20; N, 19.44. Found (%) C, 56.81; H, 4.20; N, 19.47.

EXAMPLE 11

2-Amino-4-(2,5-dichlorophenyl)-6-[2-(diethylamino)-ethylamino]-1,3,5-triazine.

Using N,N-diethylethylenediamine in lieu of diethanolamine, the procedure was carried out in the same manner as Example 1 to provide the title compound. m.p. 141–142° C.

Elemental analysis for $C_{15}H_{20}Cl_2N_6$. Calcd. (%) C, 50.71; H, 5.67; N, 23.65. Found (%): C, 50.63; H, 5.64; N, 23.50.

EXAMPLE 12

2-Amino-4-(2,5-dichlorophenyl)-6-phenethylamino-1,3,5-triazine.

Using phenethylamine in lieu of diethanolamine, the procedure was carried out in the same manner as Example 1 to provide the title compound. m.p. 217–218° C.

Elemental analysis for $C17H_{15}Cl_2N_5$. Calcd. (%): C, 56.68; H, 4.20; N, 19.44. Found (%) C, 56.94; H, 4.16; N, 19.58.

EXAMPLE 13

2-Amino-4-(2,5-dichlorophenyl)-6-(2-phenoxyethyl-amino)-1,3,5-triazine

Using 2-phenoxyethylamine in lieu of diethanolamine, the procedure was carried out in the same manner as Example 1 to provide the title compound. m.p. 172–173° C.

Elemental analysis for $C_{17}H_{15}Cl_2N_5O$. Calcd. (%) C, 54.27; H, 4.02; N, 18.61. Found (%): C, 54.45; H, 3.80; N, 18.68.

EXAMPLE 14

2-Amino-4-anilino-6-(2,5-dichlorophenyl)-1,3,5-triazine.

Using aniline in lieu of diethanolamine, the procedure was carried out in the same manner as Example 1 to provide the title compound. m.p. 180–181° C.

Elemental analysis for $C_{15}H_{11}Cl_2N_5$. Calcd. (%): C, 54.24; H, 3.34; N, 21.08. Found (%): C, 54.36; H, 3.41; N, 21.15.

EXAMPLE 15

2-Amino-4-[(carboxymethyl)amino]-6-(2,5-dichlorophenyl)-1,3,5-triazine

Using glycine in lieu of diethanolamine, the procedure was carried out in the same manner as Example 1 to provide the title compound. m.p. 271–272° C. (decomp.).

Elemental analysis for $C_{11}H_9Cl_2N_5O_2$. Calcd. (%): C, 42.06; H, 2.89; N, 22.29. Found (%) C, 42.04; H, 2.96; N, 22.23.

EXAMPLE 16

2-Amino-4-cinnamylamino-6-(2,5-dichlorophenyl)-1,3,5-triazine

Using cinnamylamine in lieu of diethanolamine, the procedure was carried out in the same manner as Example 1 to give the title compound. m.p. 198–199° C.

Elemental analysis for $C_{18}H_{15}Cl_2N_5$. Calcd. (%) C, 58.08; H, 4.06; N, 18.81. Found (%): C, 58.21; H, 4.10; N, 18.90.

EXAMPLE 17

2-Amino-4-(2-aminoethylamino)-6-(2,5-dichlorophenyl)-1,3,5-triazine.

Using ethylenediamine in lieu of diethanolamine, the procedure was carried out in the same manner as Example 1 to give the title compound. m.p. 152–153° C.

Elemental analysis for $C_{11}H_{12}Cl_2N_6$. Calcd. (%): C, 44.16; H, 4.04; N, 28.09. Found (%) C, 44.11; H, 3.93; N, 28.06.

EXAMPLE 18

2-Amino-4-(2-aminoethylamino)-6-(2,5-dichlorophenyl)-1,3,5-triazine hydrochloride Using the compound synthesized in Example 17, the title compound was obtained by the same procedure as described in Example 32 (Step 2) hereinafter. m.p. 267–268° C. (decomp.)

Elemental analysis for $C_{11}H12Cl_2N_6$. Calcd. (%): C, 39.37; H, 3.90; N, 25.04. Found (%): C, 39.04; H, 4.15; N, 24.96.

EXAMPLE 19

2-Amino-4-(2,5-dichlorophenyl)-6-[8-(3,4,5-trimethoxybenzoyloxy)octyl-1-amino]-1,3,5-triazine.

Using 8-(3,4,5-trimethoxybenzoyloxy)octylamine in lieu of diethanolamine, the procedure was carried out in the same manner as Example 1 to give the title compound. m.p. 72–73° C.

Elemental analysis for $C_{27}H_{33}Cl_2N_5O_5$. Calcd. (%) C, 56.06; H, 5.75; N, 12.11. Found (%): C, 56.09; H, 6.01; N, 12.01.

EXAMPLE 20

2-Amino-4-(2,5-dichlorophenyl)-6-(2-piperidinoethylamino)-1,3,5-triazine

Using 2-piperidinoethylamine in lieu of diethanolamine, the procedure was carried out in the same manner as Example 1 to give the title compound. m.p. 179–181° C.

Elemental analysis for $C_{16}H_{20}Cl_2N_6$. Calcd. (%): C, 52.32; H, 5.49; N, 22.88. Found (%): C, 52.12; H, 5.32; N, 22.79

EXAMPLE 21

2-Amino-4-(2,5-dichlorophenyl)-6-[4-[2-(4-methylphenoxy)ethyl]piperazin-1-yl]-1,3,5-triazine.

Using N-[2-(4-methylphenoxy)ethyl]piperazine in lieu of diethanolamine, the procedure was carried out in the same manner as Example 1 to give the title compound. m.p. 140–141° C.

Elemental analysis for $C_{22}H_{24}Cl_2N_6O$. Calcd. (%): C, 57.52; H, 5.27; N, 18.29. Found (%): C, 57.59; H, 5.27; N, 18.42.

EXAMPLE 22

2-Amino-4-(2,5-dichlorophenyl)-6-[2-(N-phenylamino)-ethylamino]-1,3,5-triazine.

Using N-phenylethylenediamine in lieu of diethanolamine, the procedure was carried out in the same manner as Example 1 to give the title compound. m.p. 139–141° C.

Elemental analysis for $C_{17}H_{16}Cl_2N_6$. Calcd. (%): C, 54.41; H, 4.30; N, 22.40. Found (%): C, 54.43; H, 4.27; N, 22.55.

EXAMPLE 23

2-Amino-4-(2,5-dichlorophenyl)-6-[4-(2-hydroxyethyl)-piperazin-1-yl]-1,3,5-triazine.

Using N-(2-hydroxyethyl)piperazine in lieu of diethanolamine, the procedure was carried out in the same manner as Example 1 to give the title compound. m.p. 185–187° C.

Elemental analysis for $C_{15}H_{18}Cl_2N_6O$. Calcd. (%): C, 48.79; H, 4.91; N, 22.76. Found (%) C, 48.63; H, 4.85; N, 22.74.

EXAMPLE 24

2-Amino-4-(2,5-dichlorophenyl)-6-(2-morpholinoethylamino)-1,3,5-triazine

Using 2-(morpholino)ethylamine in lieu of diethanolamine, the procedure was carried out in the same manner as Example 1 to give the title compound. m.p. 159–161° C.

Elemental analysis for $C_{15}H_{18}Cl_2N_6O$. Calcd. (%): C, 48.79; H, 4.91; N, 22.76. Found (%): C, 48.56; H, 4.87; N, 22.86.

EXAMPLE 25

2-Amino-4-(2,5-dichlorophenyl)-6-[4-(diphenylmethyl)-piperazin-1-yl]-1,3,5-triazine Using 1-diphenylmethylpiperazine in lieu of diethanolamine, the procedure was carried out in the same manner as Example 1 to give the title compound. m.p. 217–218° C.

Elemental analysis for $C_{26}H_{24}Cl_2N_6$. Calcd. (%): C, 63.55; H, 4.92; N, 17.10. Found (%): C, 63.68; H, 4.95; N, 17.24.

EXAMPLE 26

2-Amino-4-[2-(4-diphenylmethylpiperazin-1-yl)ethyl-amino]-6-(2,5-dichlorophenyl)-1,3,5-triazine.

Using 2-(4-diphenylmethylpiperazin-1-yl)ethylamine in lieu of diethanolamine, the procedure was carried out in the same manner as Example 1 to give the title compound. m.p. 192–193° C.

Elemental analysis for $C_{28}H_{29}Cl_2N_7 \cdot \frac{1}{2}H_2O$. Calcd. (%): C, 61.88; H, 5.56; N, 18.03. Found (%): C, 61.87; H, 5.68; N, 18.07.

EXAMPLE 27

2-Amino-4-(2,5-dichlorophenyl)-6-diethylamino-1,3,5-triazine.

Using diethylamine hydrochloride in lieu of diethanolamine, the procedure was carried out in the same manner as Example 1 to give the title compound. m.p. 137–138° C.

Elemental analysis for $C_{13}H_{15}Cl_2N_5$. Calcd. (%): C, 50.01; H, 4.84; N, 22.43. Found (%): C, 50.25; H, 4.75; N, 22.22.

EXAMPLE 28

2-Amino-4-(2,5-dichlorophenyl)-6-diisopropylamino-1,3,5-triazine.

Using diisopropylamine in lieu of diethanolamine, the procedure was carried out in the same manner as Example 1 to give the title compound. M.p. 158–159° C.

Elemental analysis for $C_{15}H_{19}Cl_2N_5$. Calcd. (%): C, 52.95; H, 5.63; N, 20.58. Found (%): C, 53.04; H, 5.53; N, 20.71.

EXAMPLE 29

2-Amino-4-[(4-carbamoylmethyl)amino]-6-(2,5-dichlorophenyl)-1,3,5-triazine

Using glycinamide hydrochloride in lieu of diethanolamine, the procedure was carried out in the same manner as Example 1 to give the title compound. m.p. 260–261° C.

Elemental analysis for $C_{11}H_{10}Cl_2N_6O \cdot \frac{1}{4}H_2O$. Calcd. (%) C, 41.59; H, 3.33; N, 26.46. Found (%) C, 41.98; H, 3.40; N, 25.74.

EXAMPLE 30

2-Amino-4-(2,5-dichlorophenyl)-6-pyrrolidino-1,3,5-triazine.

Using pyrrolidine in lieu of diethanolamine, the procedure was carried out in the same manner as Example 1 to give the title compound. m.p. 191–193° C.

Elemental analysis for $C_{13}H_{13}Cl_2N_5$. Calcd. (%): C, 50.34; H, 4.22; N, 22.58. Found (%): C, 50.35; H, 4.11; N, 22.53.

EXAMPLE 31

2-Amino-4-(2,5-dichlorophenyl)-6-(3-hydroxy-1-pyrrolidinyl)-1,3,5-triazine maleate.

(Step 1) Using 3-hydroxypyrrolidine in lieu of diethanolamine, the procedure was carried out in the same manner as Example 1 to provide 7.3 g of the free base form of the title compound.

(Step 2) In 100 ml of methanol was dissolved 7.1 g of the compound obtained in Step 1 and 2.67 g of maleic acid. This solution was concentrated to about ⅕ of its initial volume and the crystals formed were collected by filtration to provide 6.4 g of the title compound as light-yellow crystals. m.p. 192–194° C., Elemental analysis for $C_{13}H_{13}Cl_2N_5O \cdot C_4H_4O_4$. Calcd. (%): C, 46.17; H, 3.87; N, 15.84. Found (%): C, 46.05; H, 3.84; N, 15.75.

EXAMPLE 32

(S)-2-amino-4-(2,5-dichlorophenyl)-6-(2-hydroxymethyl-1-pyrrolidinyl)-1,3,5-triazine hydrochloride (Step 1) Using (S)-2-hydroxymethylpyrrolidine in lieu of diethanolamine, the procedure was carried out in the same manner as Example 1 to provide 6.2 g of the free base form of the title compound.

(Step 2) In 50 ml of methanol was dissolved 5.1 g of the compound obtained in Step 1, followed by addition of 6 ml of 20% HCl-methanol under ice-cooling. The mixture was concentrated to about ⅒ of its initial volume and the crystals formed were collected by filtration to provide 2.6 g of the title compound as white crystals. m.p. 143–145° C.

Elemental analysis for $C_{14}H_{15}Cl_2N_5O \cdot HCl \cdot H_2O$. Calcd. (%): C, 42.60; H, 4.60; N, 17.74. Found (%): C, 42.34; H, 4.61; N, 17.79.

EXAMPLE 33

(R)-2-amino-4-(2,5-dichlorophenyl)-6-(2-hydroxymethyl-1-pyrrolidinyl)-1,3,5-triazine hydrochloride.

Using (R)-2-hydroxymethylpyrrolidine in lieu of (S)-2-hydroxymethylpyrrolidine, the procedure was carried out in the same manner as Example 32 to provide the title compound. m.p. 140–143° C.

Elemental analysis for $C_{14}H_{15}Cl_2N_5O \cdot HCl \cdot H_2O$. Calcd. (%): C, 42.60; H, 4.60; N, 17.74. Found (%): C, 42.63; H, 4.59; N, 17.86.

EXAMPLE 34

2-Amino-4-(2,5-dichlorophenyl)-6-piperazino-1,3,5-triazine.

Using piperazine in lieu of diethanolamine, the procedure was carried out in the same manner as Example 1 to give the title compound. m.p. 163–165° C.

Elemental analysis for $C_{13}H_{14}Cl_2N_6$. Calcd. (%) C, 48.01; H, 4.34; N, 25.84. Found (%): C, 47.89; H, 4.21; N, 25.81.

EXAMPLE 35

2-Amino-4-(2,5-dichlorophenyl)-6-(4-phenyl-1-piperazinyl)-1,3,5-triazine.

Using N-phenylpiperazine in lieu of diethanolamine, the procedure was carried out in the same manner as Example 1 to give the title compound. m.p. 203–206° C.

Elemental analysis for $C_{19}H_{18}Cl_2N_6$. Calcd. (%) C, 56.87; H, 4.52; N, 20.94. Found (%): C, 56.77; H, 4.43; N, 20.85.

EXAMPLE 36

2-Amino-4-(2,5-dichlorophenyl)-6-(4-hydroxy-1-piperidinyl)-1,3,5-triazine.

Using 4-hydroxypiperidine in lieu of diethanolamine, the procedure was carried out in the same manner as Example 1 to give the title compound. m.p. 222–224° C.

Elemental analysis for $C_{14}H_{15}Cl_2N_5O$. Calcd. (%): C, 49.43; H, 4.44; N, 20.59. Found (%): C, 49.30; H, 4.53; N, 20.44.

EXAMPLE 37

2-Amino-4-(2,5-dichlorophenyl)-6-(3-hydroxy-1-piperidinyl)-1,3,5-triazine.

Using 3-hydroxypiperidine in lieu of diethanolamine, the procedure was carried out in the same manner as Example 1 to give the title compound. m.p. 178–180° C.

Elemental analysis for $C_{14}H_{15}Cl_2N_5O$. Calcd. (%): C, 49.43; H, 4.44; N, 20.59. Found (%): C, 49.37; H, 4.42; N, 20.57.

Example 38

2-Amino-4-(2,5-dichlorophenyl)-6-thiomorpholino-1,3,5-triazine.

Using thiomorpholine in lieu of diethanolamine, the procedure was carried out in the same manner as Example 1 to give the title compound. m.p. 239–241° C.

Elemental analysis for $C_{13}H13Cl_2N_5S$. Calcd. (%): C, 45.62; H, 3.83; N, 20.46. Found (%): C, 45.45; H, 3.66; N, 20.49.

EXAMPLE 39

2-Amino-4-(2,5-dichlorophenyl)-6-(2,6-dimethyl-4-morpholinyl)-1,3,5-triazine

Using 2,6-dimethylmorpholine in lieu of diethanolamine, the procedure was carried out in the same manner as Example 1 to give the title compound. m.p. 192–195° C.

Elemental analysis for $C_{15}H_{17}Cl_2N_5O$. Calcd. (%): C, 50.86; H, 4.84; N, 19.77. Found (%): C, 50.62; H, 4.73; N, 19.99.

EXAMPLE 40

2-Amino-4-(2,5-dichlorophenyl)-6-[4-[3-(4-methylphenoxy)propyl]-1-piperazinyl]-1,3,5-triazine.

Using N-[3-(4-methylphenoxy)propyl]piperazine in lieu of diethanolamine, the procedure was carried out in the same manner as Example 1 to give the title compound. m.p. 148–150° C.

Elemental analysis for $C_{23}H_{26}Cl_2N_6O$. Calcd. (%): C, 58.36; H, 5.54; N, 17.75. Found (%) C, 58.14; H, 5.43; N, 17.82.

EXAMPLE 41

2-Amino-4-(2,5-dichlorophenyl)-6-(3-pyrrolin-1-yl)-1,3,5-triazine.

Using 3-pyrroline in lieu of diethanolamine, the procedure was carried out in the same manner as Example 1 to give the title compound. m.p. 205–206° C.

Elemental analysis for $C_{13}H_{11}Cl_2N_5$. Calcd. (%): C, 50.67; H, 3.60; N, 22.73. Found (%): C, 50.61; H, 3.57; N, 22.69.

EXAMPLE 42

2-Amino-4-(2,5-dichlorophenyl)-6-(3-oxo-1-piperazyl)-1,3,5-triazine.

Using 2-oxopiperazine in lieu of diethanolamine, the procedure was carried out in the same manner as Example 1 to give the title compound. m.p. >275° C.

Elemental analysis for $C_{13}H_{12}Cl_2N_6O$. Calcd. (%): C, 46.04; H, 3.57; N, 24.78. Found (%): C, 45.86; H, 3.73; N, 24.60.

H-NMR (DMSO-$d_6$) δ: 3.23 (2H, bs), 3.89 (2H, bs), 4.20 (2H, S), 7.20 (2H, bs), 7.56 (2H, S), 7.73 (1H, S), 8.11 (1H, S).

EXAMPLE 43

2-Amino-4-(4-benzyl-1-piperidinyl)-6-(2,5-dichlorophenyl)-1,3,5-triazine.

Using 4-benzylpiperidine in lieu of diethanolamine, the procedure was carried out in the same manner as Example 1 to give the title compound. m.p. 159–161° C.

Elemental analysis for $C_{21}H_{21}Cl_2N_5$. Calcd. (%): C, 60.88; H, 5.11; N, 16.90. Found (%): C, 60.74; H, 5.09; N, 16.97.

EXAMPLE 44

2-Amino-4-(2,5-dichlorophenyl)-6-(hexamethyleneimin-1-yl)-1,3,5-triazine

Using hexamethyleneimine in lieu of diethanolamine, the procedure was carried out in the same manner as Example 1 to give the title compound. m.p. 155–156° C.

Elemental analysis for $C_{15}H_{17}Cl_2N_5$. Calcd. (%): C, 53.27; H, 5.07; N, 20.71. Found (%): C, 53.17; H, 4.99; N, 20.66.

EXAMPLE 45

2-Amino-4-(2,5-dichlorophenyl)-6-(2-methyl-1-piperidinyl)-1,3,5-triazine

Using 2-methylpiperidine in lieu of diethanolamine, the procedure was carried out in the same manner as Example 1 to give the title compound. m.p. 136–137° C.

Elemental analysis for $C_{15}H_{17}Cl_2N_5$. Calcd. (%): C, 53.27; H, 5.07; N, 20.71. Found (%): C, 52.81; H, 4.90; N, 20.95.

EXAMPLE 46

2-Amino-4-(2-carboxy-4-hydroxy-1-pyrrolidinyl)-6-(2,5-dichlorophenyl)-1,3,5-triazine.

Using 4-hydroxyproline in lieu of diethanolamine, the procedure was carried out in the same manner as Example 1 to give the title compound. m.p. 138–145° C.

Elemental analysis for $C_{14}H_{13}Cl_2N_5O_3 \cdot H_2O$. Calcd. (%): C, 43.32; H, 3.89; N, 18.04. Found (%): C, 43.63; H, 3.65; N, 18.17.

EXAMPLE 47

2-Amino-4-(2,5-dichlorophenyl)-6-(2-hydroxymethyl-4-hydroxy-1-pyrrolidinyl)-1,3,5-triazine.

Using 2-hydroxymethyl-4-hydroxypyrrolidine in lieu of diethanolamine, the procedure was carried out in the same manner as Example 1 to give the title compound as white powder.

Elemental analysis for $C_{14}H_{15}Cl_2N_5O_2 \cdot \frac{1}{2}EtOH \cdot \frac{1}{2}H_2O$. Calcd. (%): C, 46.40; H, 4.93; N, 18.04 Found (%): C, 46.36; H, 4.80; N, 18.24.

H-NMR (CDCl$_3$) δ: 1.7–2.0 (1H, m), 2.1–2.25 (1H, m), 2.67 (1H, bs), 3.4–3.85 (3H, m), 3.95–4.25 (1H, m), 4.35–4.55 (2H, m), 5.53 (2H, d, J=11 Hz), 7.25–7.4 (2H, m), 7.65 (1H, d, J=19 Hz).

EXAMPLE 48

2-Amino-4-(2,5-dichlorophenyl)-6-(3-hydroxymethyl-1-pyrrolidinyl)-1,3,5-triazine hydrochloride.

Using 3-hydroxymethylpyrrolidine in lieu of diethanolamine, the procedure was carried out in the same manner as Example 1. Using the resulting compound, the procedure was carried out in the same manner as Example 32 (Step 2) to provide the title compound. m.p. 241–243° C.

Elemental analysis for $C_{14}H_{15}Cl_2N_5O \cdot HCl$. Calcd. (%): C, 44.64; H, 4.28; N, 18.59. Found (%): C, 44.47; H, 4.34; N, 18.68.

EXAMPLE 49

2-Amino-4-(2,5-dichlorophenyl)-6-(4-methanesulfonyl-1-piperazinyl)-1,3,5-triazine.

Using 1-methanesulfonylpiperazine in lieu of diethanolamine, the procedure was carried out in the same manner as Example 1 to give the title compound. m.p. 184–186° C.

Elemental analysis for $C_{14}H_{16}Cl_2N_6O_2S$. Calcd. (%): C, 41.70; H, 4.00; N, 20.84. Found (%): C, 41.59; H, 3.85; N, 20.91.

EXAMPLE 50

(S)-2-amino-4-(2-carboxy-1-pyrrolidinyl)-6-(2,5-dichlorophenyl)-1,3,5-triazine

Using (S)-proline in lieu of diethanolamine, the procedure was carried out in the same manner as Example 1 to give the title compound. m.p. 144–147° C.

Elemental analysis for $C_{14}H_{13}Cl_2N_5O_2$. Calcd. (%) C, 47.47; H, 3.70; N, 19.77. Found (%): C, 47.59; H, 3.88; N, 19.77.

EXAMPLE 51

2-Amino-4-(2,5-dichlorophenyl)-6-(3-methanesulfonyl-amino-1-pyrrolidinyl)-1,3,5-triazine.

Using 3-methanesulfonylaminopyrrolidine in lieu of diethanolamine, the procedure was carried out in the same manner as Example 1 to give the title compound. m.p. 102–107° C.

Elemental analysis for $C_{14}H_{16}Cl_2N_6O_2S \cdot \frac{1}{2}CH_3OH \cdot \frac{1}{2}CHCl_3$. Calcd. (%): C, 39.44; H, 3.98; N, 18.71. Found (%): C, 39.77; H, 3.90; N, 18.77.

EXAMPLE 52

2-Amino-4-(2,5-dichlorophenyl)-6-(3-hydroxy-1-azetidinyl)-1,3,5-triazine.

Using 3-hydroxyazetidine in lieu of diethanolamine, the procedure was carried out in the same manner as Example 1 to give the title compound. m.p. 256–257° C.

Elemental analysis for $C_{12}H_{11}Cl_2N_5O$. Calcd. (%): C, 46.17; H, 3.55; N, 22.44. Found (%): C, 45.93; H, 3.48; N, 22.03.

EXAMPLE 53

2-Amino-4-(2,5-dichlorophenyl)-6-(3-hydroxymethyl-1-azetidinyl)-1,3,5-triazine.

Using 3-hydroxymethylazetidine in lieu of diethanolamine, the procedure was carried out in the same manner as Example 1 to give the title compound. m.p. 224–226° C.

Elemental analysis for $C_{13}H_{13}Cl_2N_5O$. Calcd. (%) C, 47.87; H, 4.02; N, 21.47. Found (%): C, 47.67; H, 3.88; N, 21.15.

EXAMPLE 54

2-Amino-4-(2-carboxy-1-piperidinyl)-6-(2,5-dichlorophenyl)-1,3,5-triazine.

Using 2-carboxypiperidine in lieu of diethanolamine, the procedure was carried out in the same manner as Example 1 to give the title compound. m.p. 237–240° C.

Elemental analysis for $C_{15}H_{15}Cl_2N_5O_2$. Calcd. (%) C, 48.93; H, 4.11; N, 19.02. Found (%): C, 48.58; H, 4.19; N, 18.79.

EXAMPLE 55

2-Amino-4-(2,5-dichlorophenyl)-6-(4-hydroxy-4-phenyl-1-piperidinyl)-1,3,5-triazine.

Using 4-hydroxy-4-phenylpiperidine in lieu of diethanolamine, the procedure was carried out in the same manner as Example 1 to give the title compound. m.p. 176–178° C.

Elemental analysis for $C_{20}H_{19}Cl_2N_5O$. Calcd. (%): C, 57.70; H, 4.60; N, 16.82. Found (%): C, 57.54; H, 4.58; N, 16.76.

EXAMPLE 56

2-Amino-4-(2,5-dichlorophenyl)-6-(4-oxo-1-piperidinyl)-1,3,5-triazine.

Using 4-oxopiperidine in lieu of diethanolamine, the procedure was carried out in the same manner as Example 1 to give the title compound. m.p. 223–225° C.

EXAMPLE 57

2-Amino-4-(2,5-dichlorophenyl)-6-(4-hydroxymethyl-1-piperidinyl)-1,3,5-triazine.

Using 4-hydroxymethylpiperidine in lieu of diethanolamine, the procedure was carried out in the same manner as Example 1 to give the title compound. m.p. 173–175° C.

Elemental analysis for $C_{15}H_{17}Cl_2N_5O$. Calcd. (%): C, 50.86; H, 4.84; N, 19.77. Found (%): C, 50.79; H, 4.80; N, 19.74.

EXAMPLE 58

2-Amino-4-(2,5-dichlorophenyl)-6-(1-oxothiomorpholin-4-yl)-1,3,5-triazine.

In 150 ml of acetic acid was dissolved 2.0 g of the compound synthesized in Example 38. To this solution was added 1.3 ml of 30% aqueous solution of hydrogen peroxide dropwise under ice-cooling and the mixture was stirred at the same temperature for 3 hours. The excess of hydrogen peroxide was decomposed with aqueous sodium sulfite solution and the mixture was concentrated. The crystals separated out were collected by filtration, rinsed with water, and dried to provide 1.86 g of the title compound as white crystals. m.p. 267–269° C.

Elemental analysis for $C_{13}H_{13}Cl_2N_5OS$. Calcd. (%) C, 43.58; H, 3.66; N, 19.55. Found (%): C, 43.21; H, 3.58; N, 19.24.

EXAMPLE 59

2-Amino-4-(2,5-dichlorophenyl)-6-(1,1-dioxothiomorpholin-4-yl)-1,3,5-triazine.

In 150 ml of acetic acid was dissolved 2.0 g of the compound synthesized in Example 38. To this solution was added 2.5 ml of 30% aqueous solution of hydrogen peroxide dropwise under ice-cooling and the mixture was stirred at 50° C. for 6 hours. The crystals separated out were collected by filtration, rinsed with methanol, and dried to provide 1.84 g of the title compound as white crystals. m.p. >275° C.

Elemental analysis for $C_{13}H_{13}Cl_2N_5O_2S$. Calcd. (%) C, 41.72; H, 3.50; N, 18.71. Found (%): C, 41.80; H, 3.50; N, 18.67.

H-NMR (DMSO-$d_6$) δ: 3.1–3.25 (2H, m), 4.1–4.25 (2H, m), 7.2–7.35 (2H, bs), 7.56 (2H, S), 7.73–7.75 (1H, m).

EXAMPLE 60

1,5-Dideoxy-1,5-[[2-amino-4-(2,5-dichlorophenyl)-1,3,5-triazin-6-yl]imino]-D-glucitol Using 1,5-dideoxy-1,5-imino-D-glucitol in lieu of diethanolamine, the procedure was carried out in the same manner as Example 1 to give the title compound as white powders.

Elemental analysis for $C_{15}H_{17}Cl_2N_5O_4 \cdot \frac{1}{2}C_2H_5OH \cdot \frac{3}{10}H_2O$. Calcd. (%): C, 44.62; H, 4.82; N, 16.26. Found (%): C, 44.65; H, 4.99; N, 16.32.

H-NMR (DMSO-$d_6$) δ: 3.29–3.38 (1H, m), 3.49–3.54 (1H, m), 3.58–3.66 (2H, m), 3.74–3.82 (2H, m), 4.45–4.57 (2H, m), 4.67 (1H, t, J=5 Hz), 4.89–4.96 (2H, m), 5.19–5.21 (1H, m), 6.85–7.05 (2H, bs), 7.53–7.58 (2H, m), 7.69–7.70 (1H, m).

EXAMPLE 61

2-Amino-4-(2,5-dichlorophenyl)-6-(1-azetidinyl)-1,3,5-triazine.

Using azetidinine in lieu of diethanolamine, the procedure was carried out in the same manner as Example 1 to give the title compound. m.p. 207–208° C.

Elemental analysis for $C_{12}H_{11}Cl_2N_5$. Calcd. (%): C, 48.67; H, 3.74; N, 23.65. Found (%): C, 48.58; H, 3.66; N, 23.63.

EXAMPLE 62

2-Amino-4-(2,5-dichlorophenyl)-6-(3-aminomethyl-1-pyrrolidinyl)-1,3,5-triazine dihydrochloride.

Using 3-(t-butoxycarbonylaminomethyl)pyrrolidine in lieu of diethanolamine, the procedure was carried out in the same manner as Example 1. The resulting compound (6.3 g) was dissolved in 60 ml of methanol and while the solution was stirred under ice-cooling, 20 ml of 30% HCl/CH$_3$OH was added, and was then stirred for 2 hours. The crystals formed were collected by filtration to provide 4.18 g of the title compound. m.p. >275° C.

Elemental analysis for C$_{14}$H$_{16}$Cl$_2$N$_6$.2HCl.2H$_2$O. Calcd. (%) C, 37.52; H, 4.95; N, 18.75. Found (%): C, 37.60; H, 4.96; N, 18.93.

H-NMR (DMSO-d$_6$) δ: 1.7–1.95 (1H, m), 2.05–2.3 (1H, m), 2.5–2.8 (1H, m), 2.92 (2H, bs), 3.25–3.45 (1H, m), 3.45–3.65 (1H, m), 3.65–4.0 (2H, m), 7.68 (2H, s), 7.83 (1H, s), 8.31 (3H, bs).

EXAMPLE 63

2-Amino-4-(2,5-dichlorophenyl)-6-(3-methanesulfonylaminomethyl-1-pyrrolidinyl)-1,3,5-triazine hydrochloride.

In 40 ml of THF was dissolved 2.1 g of the free base obtained by neutralizing the compound of Example 62, followed by addition of 0.94 g of potassium carbonate and 0.78 g of methanesulfonyl chloride. The mixture was reacted at room temperature for 20 hours. The THF was removed by concentration and the residue was diluted with water and extracted with chloroform. The extract was washed with water and dried and the chloroform was distilled off. The residue was purified by silica gel column chromatography (elution with CHCl$_3$:MeOH=19:1) and the resulting oil, 2.3 g, was treated in the same manner as in Example 32 (Step 2) to provide the title compound. m.p. 220–230° C.

Elemental analysis for C$_{15}$H$_{18}$Cl$_2$N$_6$O$_2$S.HCl.½H$_2$O. Calcd. (%): C, 38.93; H, 4.36; N, 18.16. Found (%): C, 38.64; H, 4.13; N, 17.92.

REFERENCE EXAMPLE 4

2-Amino-4-(2,5-dichlorophenyl)-6-piperidino-1,3,5-triazine.

Using piperidine in lieu of diethanolamine, the procedure was carried out in the same manner as Example 1 to give the title compound. m.p. 192–194° C.

Elemental analysis for C$_{14}$H$_{15}$Cl$_2$N$_5$. Calcd. (%): C, 51.87; H, 4.66; N, 21.60. Found (%): C, 51.86; H, 4.65; N, 21.64.

REFERENCE EXAMPLE 5

2-Amino-4-(2,5-dichlorophenyl)-6-morpholino-1,3,5-triazine.

Using morpholine in lieu of diethanolamine, the procedure was carried out in the same manner as Example 1 to give the title compound. m.p. 189–191° C.

Elemental analysis for C$_{13}$H$_{13}$Cl$_2$N$_5$O. Calcd. (%): C, 47.87; H, 4.02; N, 21.47. Found (%): C, 47.85; H, 3.92; N, 21.52.

TEST EXAMPLE 1

Antihepatitis effect:

The antihepatitis action of the compound of the invention could be confirmed by the following test in mice. This test is the commonest animal test for evaluating the antihepatitis effect of drugs. It is known that the antihepatitis effect evaluated by this test method is highly correlated with the clinical effect in man (Kondo, Y. et al. Chem. Pharm. Bull. 38, 2887–2889, 1990).

Method: Six-week-old male BALB/C mice were intravenously dosed with 1 mg of BCG and after 2 weeks, 50 mg/kg of the test drug was administered orally. Then, after 1 hour, 2.5 μg of lipopolysaccharide (LPS) was injected intravenously to induce hepatitis. To find the LPS-associated mortality, the percentage of deaths at 48 hours was calculated. The mortality in the control group was 80–100%. The plasma transaminase (GOT, GPT) levels are known to start rising about 8 hours after LPS administration and actually no sufficient elevation was noted at 4 hours. However, for reference's sake, blood was drawn from the orbital vein at hour 4 and the plasma transaminase (GOT, GPT) concentrations were determined. As a reference compound, 2,4-diamino-6-(2,5-dichlorophenyl)-1,3,5-triazine was used. The results are presented in Table 1.

TABLE 1

Inhibitory effect on BCG-LPS-induced fulminant hepatitis in mice

| Test drug (Example No.) | Number of deaths/ number of animals/used | % Inhibition GOT | GPT |
|---|---|---|---|
| Example 1 | 2/10** | 37** | 17 |
| Example 2 | 0/10** | 46** | 33* |
| Example 3 | 0/10** | 37** | 38 |
| Example 5 | 0/10** | 43** | 18 |
| Example 6 | 2/10** | 34** | 29 |
| Example 21 | 0/10** | 29** | 10 |
| Example 30 | 0/18** | 45** | 31** |
| Example 31 | 1/18** | 47** | 34** |
| Example 32 | 0/18** | 62** | 60** |
| Example 33 | 0/18** | 39* | 41* |
| Example 37 | 0/18** | 43** | 38* |
| Example 56 | 0/15** | 38** | 37** |
| Example 62 | 0/15** | 29* | 38** |
| Reference Example 5 | 0/18** | 58** | 45** |
| Reference Compound | 0/10* | 21 | −6 |

*p < 0.05
**p < 0.01

The compound of the present invention showed substantially the same death-inhibitory effect as the reference compound and inhibited elevation of serum transaminase levels, which are indicators of liver disorder, in a remarkable measure.

Thus, the compound of the present invention has potent antihepatitis activity and is, therefore, useful for the therapy and prophylaxis of hepatitis.

TEST EXAMPLE 2

Inhibitory effect on hepatic chemooncogenesis Method: Five-week-old male F344 rats (Slc), a precancerous lesion model was constructed using the following protocol in accordance with the method of Solt and Faber (Nature, 263, 702–703, 1976).

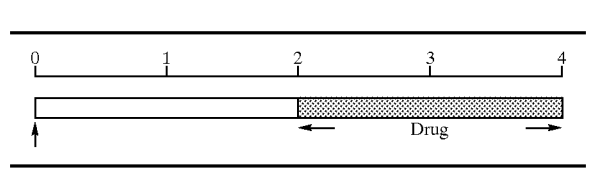

DEN 200 mg/kg, i.p.

:

70% hepatectomy

:

0.02% AAF

:

Diet or water

←→:

Drug administration period

Thus, the duration of the experiment being set at 4 weeks, 200 mg/kg of diethylnitrosoamine (hereinafter referred to briefly as DEN) was first administered intraperitoneally. Beginning week 2, drinking water containing 0.02% of 2-acetylaminofluorene (hereinafter referred to briefly as AAF) was given ad libitum. At the beginning of week 3, 70% hepatectomy was performed. The test drug was mixed into the animal chow (F-2, Funabashi Farm) at the concentration of 0.01% and administered from week 2 through the final day of the experiment. The compound of Example 1 was used as the test drug and 2,4-diamino-6-(2,5-dichlorophenyl)-1,3,5-triazine as the reference compound.

On the final day of the experiment, all the animals were sacrificed by cervical dislocation under ether anaesthesia. Immediately a portion of the liver was excised, quick-frozen in dry ice-acetone, and stored until used. From the liver, 8 μm-thick frozen sections were prepared and using Vectastain ABC Kit (Funakoshi Yakuhin), immunostained by the ABC method (an enzyme-labeled antibody method) using anti-glutathione-S-transferase placental form (hereinafter referred to briefly as GST-P) antibody as the primary antibody. Thus, sections were returned to room temperature under anhydrous conditions and immersed in 10 mM phosphate-buffered saline (hereinafter referred to briefly as PBS) at pH 7.2 for 15 minutes. Then, goat normal serum and the primary antibody (a 500-fold dilution, 20 μl) were applied to the section and allowed to react overnight. After the reaction, the section was washed with PBS. Then, anti-rabbit secondary antibody was applied and the reaction was carried out for 30 minutes. After washing with PBS, avidin-biotin complex was applied and allowed to react for 30 minutes. The section was washed with PBS and treated with 0.1% diaminobenzidine (DAB) containing 0.02% of hydrogen peroxide for color development, dehydrated, and sealed.

The number of GST-P-positive lesions per $cm^2$ liver tissue section was counted under an optical microscope and the area was measured with an image analyzer (SPICCA-II, Japan Avionics). The significance testing of mean values was made by Student's t-test and the result was evaluated at the 5% leval of significance. The results are presented in Table 2.

TABLE 2

Inhibitory effect on hepatic chemooncogenesis in rats

| Test drug (Example No.) | n | GST-P+ foci (N/$cm^2$) mean ± S.E. | inhibition (%) | GST-P+ area ($mm^2$/$cm^2$) mean ± S.E. | inhibition (%) |
|---|---|---|---|---|---|
| Control | 10 | 58.4 ± 6.7 | — | 1.5 ± 0.3 | — |
| Example 1 | 10 | 41.5 ± 5.2 | 28.9 | 0.8 ± 0.2 | 48.6 |
| Control | 6 | 75.2 ± 16.3 | — | 3.9 ± 0.7 | — |
| Refer.Compd. | 8 | 67.9 ± 8.7 | 9.7 | 3.6 ± 0.7 | 7.7 |

The compound of the present invention, at a concentration of 0.01%, decreased the number and area of GST-P-positive lesions. The inhibition rates were 28.9% and 48.6%, respectively. On the other hand, 0.01% of the reference compound showed no inhibitory effect on the number of GST-P-positive lesions (inhibition rate 9.7%) or on the area of lesions (inhibitory rate 7.7%).

TEST EXAMPLE 3

Acute Toxicity

Rats of either sex (SD strain, 280–360 g) were used in groups of 5. The animals were deprived of food from the previous day (16–18 hours before) and 1 g/kg of the compound of Example 1 was administered orally by gastric gavage. Then, deaths during the subsequent one-week period were recorded. As a result, no death was found at all.

Thus, the toxicity of the compound of the invention is very low.

TEST EXAMPLE 4

Effect on body weight gain:

The compound of Example 1 was administered to rats daily to investigate its effect on body weight gain.

Even at 1,000 mg/kg administered repeatedly, the compound of the present invention did not affect body weight gain.

FORMULATION EXAMPLE 1

The compound of Example 1 (2 g) is mixed with 70 g of lactose and 30 g of corn starch thoroughly. Following addition of 25 ml of 16% hydroxypropylcellulose solution, the mixture is stirred-granulated. The granules thus obtained are dried, sieving, and mixed with 2 g of magnesium stearate and 2 g of talc, and the whole composition is compressed with a rotary tablet machine to provide tablets.

Formula: 110 mg per tablet

| Compound of Example 1 | 2 mg |
|---|---|
| Lactose | 70 mg |
| Corn starch | 30 mg |
| Hydroxypropylcellulose | 4 mg |
| Magnesium stearate | 2 mg |
| Talc | 2 mg |

FORMULATION EXAMPLE 2

To 4 mg of the compound of Example 1 is added 996 mg of lactose and the mixture is evenly blended to provide powders.

INDUSTRIAL APPLICABILITY

The compound of the present invention has potent anti-hepatitis activity as well as hepatic oncogenesis inhibitory activity which is not found in the reference drug irsogladine maleate and is a safe compound with a low toxic potential. Therefore, the compound is useful as a medicine for the therapy and prophylaxis of hepatitis in mammals inclusive of man.

We claim:

1. A compound of the following general formula [I] or a salt thereof, or a hydrate or an ethanolate thereof,

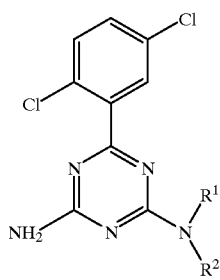

[I]

wherein $R^1$ and $R^2$ may be the same or different and each represents (1) hydrogen, (2) substituted alkyl, (3) unsubstituted or substituted aralkyl, (4) unsubstituted or substituted aralkenyl, or (5) unsubstituted or substituted aryl, or $R^1$ and $R^2$, jointly and taken together with the adjacent N atom, represent a 4- through 8-membered cyclic amino group of the formula $NR^1R^2$; the cyclic amino group may further contain, nitrogen, oxygen, or sulfur as a ring member and is substituted; provided, that the case in which both of $R^1$ and $R^2$ represent hydrogen and the case in which $NR^1R^2$ forms an unsubstituted ring are excluded.

2. The compound according to claim 1 wherein $R^1$ and $R^2$ may be the same or different and each represents (1) hydrogen, (2) alkyl that is substituted by a substituent group selected from the group consisting of hydroxy, alkoxy, amino, monoalkylamino, dialkylamino, arylamino, 4-through 8-membered cyclic amino, carboxy, carbamoyl, aryloxy, and aroyloxy, (3) aralkyl, (4) aralkenyl, or (5) aryl.

3. The compound according to claim 1 wherein $NR^1R^2$ represents a 4- through 8-membered cyclic amino group that is substituted by a substituent group selected from the group consisting of hydroxy, oxo, carboxy, alkyl, hydroxyalkyl, aryloxyalkyl, aminoalkyl, alkylsulfonylaminoalkyl, alkylsulfonylamino, alkylsulfonylaralkyl, alkylsulfonyl, aryl, aralkyl, 2-pyrimidyl, and cyclic amino.

4. The compound according to claim 1 wherein $R^1$ and $R^2$ may be the same or different and each represents hydroxyalkyl or $NR^1R^2$ represents pyrrolidino, piperidino, or morpholino that may be substituted.

5. The compound according to claim 1 wherein $R^1$ and $R^2$ may be the same or different and each represents hydroxyalkyl or $NR^1R^2$ represents pyrrolidino, piperidino, or morpholino that is substituted by hydroxy, hydroxyalkyl, oxo, alkyl, amino, or aminoalkyl.

6. The compound according to claim 1, wherein $R^1$ and $R^2$, when taken together with the nitrogen atom to which they are attached, form pyrrolidino substituted by one or two substituents selected from hydroxy and hydroxyalkyl.

7. A method for the treatment of mammals, including humans, suffering from hepatitis, which comprises administering to said sufferer an antihepatitis effective amount of a compound of formula [I] or a pharmaceutically acceptable salt thereof or a hydrate or an ethanolate thereof,

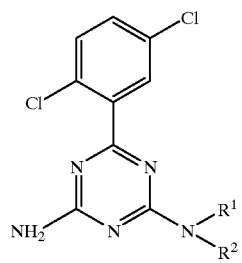

[I]

wherein $R^1$ and $R^2$ may be the same or different and each represents hydrogen, unsubstituted or substituted alkyl, aralkyl, aralkenyl, or aryl, or $R^1$ and $R^2$ taken together with the nitrogen atom to which they are attached form unsubstituted or substituted cyclic amino having 4 to 8 ring members, said cyclic amino containing the depicted nitrogen atom as the sole heteroatom or containing nitrogen, oxygen, or sulfur as a second heteroatom; provided, however, that when one of $R^1$ and $R^2$ is hydrogen the other may not be hydrogen.

8. The method according to claim 7, wherein $R^1$ and $R^2$ may be the same or different and each represents hydrogen; unsubstituted alkyl; alkyl substituted by hydroxy, alkoxy, amino, monoalkylamino, dialkylamino, arylamino, 4 to 8-membered cyclic amino, carboxy, carbamoyl, aryloxy or aroyloxy; aralkyl; aralkenyl; or aryl.

9. The method according to claim 7, wherein $NR^1R^2$ represents said 4- to 8-membered cyclic amino, said 4- to 8-membered cyclic amino being unsubstituted or substituted by hydroxy, oxo, carboxy, alkyl, hydoxyalkyl, aryloxyalkyl, aminoalkyl, alkylsulfonylaminoalkyl, alkylsulfonylamino, alkylsulfonylaralkyl, alkylsulfonyl, aryl, aralkyl, 2-pyrimidyl or 4- to 8-membered cyclic amino.

10. The method according to claim 7, wherein $R^1$ and $R^2$ each represents hydroxyalkyl or $R^1$ and $R^2$ when taken together with the nitrogen atom to which they are attached form unsubstituted or substituted pyrrolidino, piperidino, piperazino or morpholino.

11. The method according to claim 7, wherein $R^1$ and $R^2$ each represents hydroxyalkyl or $R^1$ and $R^2$ when taken together with the nitrogen atom to which they are attached form unsubstituted pyrrolidino, piperidino, piperazino or morpholino; or pyrrolidino, piperidino, piperazino or morpholino substituted by hydroxy, hydroxyalkyl, oxo, alkyl, amino or aminoalkyl.

12. The method according to claim 10, wherein $R^1$ and $R^2$ when taken together with the nitrogen atom to which they are attached form pyrrolidino substituted by one or two substituents selected from hydroxy and hydroxyalkyl.

13. A composition for the treatment of mammals, including humans, suffering from hepatitis, which comprises a therapeutically effective amount for the treatment of hepatitis of a compound of formula [I] or a pharmaceutically acceptable salt thereof or a hydrate or an ethanolate thereof together with a pharmaceutically acceptable carrier therefor:

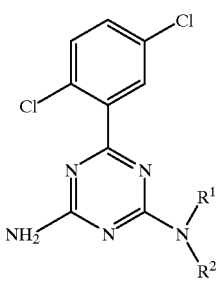

wherein $R^1$ and $R^2$ may be the same or different and each represents hydrogen, unsubstituted or substituted alkyl, aralkyl, aralkenyl, or aryl, or $R^1$ and $R^2$ taken together with the nitrogen atom to which they are attached form unsubstituted or substituted cyclic amino having 4 to 8 ring members, said cyclic amino containing the depicted nitrogen atom as the sole heteroatom or containing nitrogen, oxygen, or sulfur as a second heteroatom; provided, however, that when one of $R^1$ and $R^2$ is hydrogen the other may not be hydrogen.

14. The composition according to claim 13, wherein $R^1$ and $R^2$ may be the same or different and each represents hydrogen; unsubstituted alkyl; alkyl substituted by hydroxy, alkoxy, amino, monoalkylamino, dialkylamino, arylamino, 4 to 8-membered cyclic amino, carboxy, carbamoyl, aryloxy or aroyloxy; aralkyl; aralkenyl; or aryl.

15. The composition according to claim 13, wherein $NR^1R^2$ represents said 4- to 8-membered cyclic amino, said 4- to 8-membered cyclic amino being unsubstituted or substituted by hydroxy, oxo, carboxy, alkyl, hydoxyalkyl, aryloxyalkyl, aminoalkyl, alkylsulfonylaminoalkyl, alkylsulfonylamino, alkylsulfonylaralkyl, alkylsulfonyl, aryl, aralkyl, 2-pyrimidyl or 4- to 8-membered cyclic amino.

16. The composition according to claim 13, wherein $R^1$ and $R^2$ each represents hydroxyalkyl or $R^1$ and $R^2$ when taken together with the nitrogen atom to which they are attached form unsubstituted or substituted pyrrolidono, piperidino, piperazino or morpholino.

17. The composition according to claim 13, wherein $R^1$ and $R^2$ each represents hydroxyalkyl or $R^1$ and $R^2$ when taken together with the nitrogen atom to which they are attached form unsubstituted pyrrolidino, piperidino, piperazino or morpholino; or pyrrolidino, piperidino, piperazino or morpholino substituted by hydroxy, hydroxyalkyl, oxo, alkyl, amino or aminoalkyl.

18. The composition according to claim 13, wherein $R^1$ and $R^2$ when taken together with the nitrogen atom to which they are attached form pyrrolidino substituted by one or two substituents selected from hydroxy and hydroxyalkyl.

* * * * *